United States Patent
Novikov et al.

(10) Patent No.: US 6,841,389 B2
(45) Date of Patent: Jan. 11, 2005

(54) METHOD OF DETERMINING CONCENTRATION OF GLUCOSE IN BLOOD

(75) Inventors: Igor A. Novikov, St. Petersburg (RU); Alexander V. Kislov, St. Petersburg (RU)

(73) Assignee: GlucoSens, Inc., Boston, MA (US)

( * ) Notice: Subject to any disclaimer, the term of this patent is extended or adjusted under 35 U.S.C. 154(b) by 437 days.

(21) Appl. No.: 10/068,603

(22) Filed: Feb. 5, 2002

(65) Prior Publication Data

US 2002/0155615 A1 Oct. 24, 2002

Related U.S. Application Data

(60) Provisional application No. 60/266,774, filed on Feb. 5, 2001.

(51) Int. Cl.$^7$ ............................................. G01N 33/00
(52) U.S. Cl. ........................ 436/95; 436/149; 436/150
(58) Field of Search ........................ 436/95, 149, 150

(56) References Cited

U.S. PATENT DOCUMENTS

| | | | | |
|---|---|---|---|---|
| 5,725,480 A | * | 3/1998 | Oosta et al. ................. | 600/310 |
| 5,752,512 A | * | 5/1998 | Gozani ........................ | 600/347 |
| 5,890,489 A | * | 4/1999 | Elden .......................... | 128/898 |
| 6,517,482 B1 | * | 2/2003 | Elden et al. ................ | 600/309 |
| 2003/0220581 A1 | * | 11/2003 | Ollmar et al. ............... | 600/547 |

FOREIGN PATENT DOCUMENTS

WO    WO 99/39627    8/1999    ............ A61B/5/00

* cited by examiner

*Primary Examiner*—Yelena Gakh
(74) *Attorney, Agent, or Firm*—Houston Eliseeva LLP

(57) ABSTRACT

A method of non-invasive determination of a glucose concentration in blood based on the measurements of the total impedance of the skin of a patient is disclosed. The method is based on a linear model of a first order correlation between the glucose concentration and the total impedance, the model taking into account the rate of change of the glucose concentration. The coefficients used in an approximating function are determined at the preliminary stage measurements by an invasive method.

18 Claims, 4 Drawing Sheets

METHOD OF DETERMINING CONCENTRATION OF GLUCOSE IN BLOOD

This application claims priority from a U.S. provisional patent application Ser. No. 60/266,774, filed Feb. 5, 2001, which is incorporated herein by reference.

BACKGROUND OF THE INVENTION

The present invention relates to non-invasive methods of medical examination of a patient. In particular, the present invention relates to an impedance-based method of determining the concentration of glucose in blood.

Some of the non-invasive methods of determining the concentration of glucose in blood are based on measuring total electrical resistance (impedance) or a component of the total resistance of a body part of a patient. For example, Russian patent 2073242 describes a method of indicating the level of sugar in blood based on the changes in the dielectric permeability of a finger placed in the electrical field. In another example, described in Russian patent 2088927, the determination of the glucose concentration in blood was accomplished by varying the reactive impedance of the oscillating circuits. In particular, the effect of a human being on the reactive impedance of the oscillating circuits plugged into the secondary circuits of the high frequency generator was measured and the concentration of sugar in blood was monitored based on the changes of the current in the secondary circuits. In yet another example, such as U.S. Pat. No. 5,792,668, the method comprises performing a spectral analysis of the high frequency radiation reflected from a or transmitted through a human body. The measured parameter in that method was a phase difference between the incoming radiation and either reflected or transmitted radiation, characteristic a component of the total resistance of a human body. In yet another example, a device described in a Russian Certificate for a Utility Model #9703, a determination of the glucose concentration in blood was based on measuring the total resistance of a part of a human body using two different frequencies, determining a capacitive component of the total resistance and then converting the determined value of the capacitive component into a level of glucose in the blood of a patient.

All the above-described methods have a common disadvantage in that the accuracy of the measurements of glucose in blood is inferior to that of the invasive methods. On the other hand, the invasive methods always require taking a blood sample, which is undesirable from the viewpoint of safety and convenience. The above-described methods are based on the determination of the total or reactive resistance (or the components of the resistance) of a part of a human body and are not very accurate.

It is therefore desirable to provide a simple and accurate non-invasive method of determining a glucose concentration in blood, which method will later become the basis for individual glucose test kits.

SUMMARY OF THE INVENTION

It has been discovered that the total electrical impedance of a human body, as well as the components of the total electrical impedance, depend not only on the actual value of the concentration of glucose in blood, but also on the temporal rate of change of that concentration. The rate of change of the glucose concentration is specific to each individual and varies within certain limits depending on a number of reasons and factors, such as, for example, environmental, psycho-physiological, nutritional, specific metabolic factors and others.

Moreover, the rate of change of the glucose concentration even for a specific individual can have different values depending on whether the concentration of glucose is higher or lower than the so-called "renal threshold". The relevance of the "renal threshold" to the determination of the glucose concentration in blood is explained by the fact that when the concentration exceeds a certain level (7–9 mmol/l for children, 8–11 mmol/l for adults), kidneys begin to produce glucose, which glucose is later discharged from the body with urine. Those threshold values of the glucose concentration characteristic to each individual within the specified limits are called the "renal threshold".

The present invention provides at least two embodiments of the method of measuring the glucose concentration in blood. The first embodiment is based on discreet measurements, the second embodiment is based on continuous measurements.

According to the first embodiment, the method of determining the concentration of glucose in blood comprises measuring the total impedance or a component of the total impedance of the skin and then determining the concentration of glucose in accordance with the following equation:

$$G(t) = G_1 e^{-a_0 t} + q + a_1 e^{-a_0 t} \int_0^t N(x) e^{a_0 x} dx,$$

wherein G(t) is the concentration of glucose in blood at time t;

$G_0$ is the initial concentration of glucose in blood at the beginning of the measurement process;

q is a parameter that characterizes the ability of a human organism to maintain homeostasis relative to the concentration of glucose in blood (it should be noted that for healthy people q is a non-zero value, while for the insulin-dependent people q is close to zero);

$G_1 = G_0 - q$;

$a_0$ is a coefficient that characterizes the correlation between a total electrical impedance (or its components) of the skin and a concentration of glucose in blood of a specific individual;

$a_1$ is a coefficient taking into account the variability of the external factors and specific characteristics of an individual;

N(x) corresponds to the normalized measured values of the total electrical impedance of the skin or the measured components of the total electrical impedance of the skin.

Parameter q and coefficients $a_0$ and $a_1$ are determined at the preliminary measurement stage. At the preliminary stage the concentration of glucose in blood is measured by an invasive method during time period T simultaneously with the measurements of the total impedance of the skin (or a component of the total impedance). Parameters q, $a_0$ and $a_1$ are determined by approximating the measured glucose concentration values in accordance with the above-described expression for G(t). Time T is selected to be sufficient to record the changes of the concentration of glucose related to the natural daily cyclical variations of glucose as well as the changes related to a diet, exercise, glucose or insulin injections.

To increase the accuracy of the approximation at the preliminary stage, the above-described measurements are performed during the increase as well as the decrease of the glucose concentration in blood. In particular, q, $a_0$ and $a_1$ are determined at the glucose concentration levels lower than the renal threshold, higher than the renal threshold, and approximately equal to the renal threshold.

The measured components of the total impedance of the skin can be the following: an active component, a reactive component, or a phase angle between the active and reactive components of the total impedance. In particular, for an individual depending on insulin, parameter q is chosen to be zero. Additionally, the method in accordance with the above-described first embodiment calls for the preliminary measurement time period T from about 4 hours to about 12 hours.

According to the second embodiment of the invention, the measurements of the total impedance of the skin (or components of the total impedance) are taken discreetly, in which case the glucose concentration is determined as follows:

$$G(t_m) = G_1 e^{-a_0 t_m} + q + a_1 e^{-a_0 t_m} \sum_{k=1}^{m} [N(t_k)e^{a_0 t_k} + N(t_{k-1})e^{a_0 t_{k-1}}]\frac{(t_k - t_{k-1})}{2},$$

wherein $G(t_m)$ is the concentration of glucose in blood at time $t_m$;

$G_0$ is the initial concentration of glucose in blood at the beginning of the measurement process;

q—a parameter that characterizes the ability of a human organism to maintain homeostasis relative to the concentration of glucose in blood (it should be noted that for healthy people q is a non-zero value, while for the insulin-dependent people q is close to zero);

$$G_1 = G_0 - q;$$

$a_0$ is a coefficient that characterizes the correlation between total electrical impedance (or its components) of the skin and a concentration of glucose in blood of a specific individual;

$a_1$ is a coefficient taking into account the variability of the external factors and specific characteristics of an individual;

$N(t_k)$ are the normalized measured values of the total impedance (or its components) of the skin, where $t_{k-1}$ and $t_k$ correspond to the times of the discreet measurements, starting with the initial measurement at $t_0=0$, k corresponds to an integer (k=1, 2, . . . m). Similar to the described first embodiment of the invention, q, $a_0$ and $a_1$ are determined at the preliminary measurement stage. At the preliminary stage the concentration of glucose in blood is measured by an invasive method during time period T simultaneously with the measurements of the total impedance of the skin (or a component of the total impedance). Parameters q, $a_0$ and $a_1$ are determined by approximating the measured glucose concentration values in accordance with the above-described expression for $G(t_m)$. Time T is selected to be sufficient to record the changes of the concentration of glucose related to the natural daily cyclical variations of glucose as well as the changes related to a diet, exercise, glucose or insulin injections.

As in the first embodiment, to increase the accuracy of the approximation at the preliminary stage, the above-described measurements are performed during the increase as well as the decrease of the glucose concentration in blood. In particular, q, $a_0$ and $a_1$ are determined at the glucose concentration levels lower than the renal threshold, higher than the renal threshold, and approximately equal to the renal threshold.

The measured components of the total impedance of the skin can be the following: an active component, a reactive component, or a phase angle between the active and reactive components of the total impedance. In particular, for an individual depending on insulin, parameter q is chosen to be zero. Additionally, the method in accordance with the above-described first embodiment calls for the preliminary measurement time period T from about 4 hours to about 12 hours.

The present invention provides for a much better accuracy of the determination of the glucose concentration in blood.

BRIEF DESCRIPTION OF THE DRAWING FIGURES

DETAILED DESCRIPTION OF THE INVENTION

Figure 1:
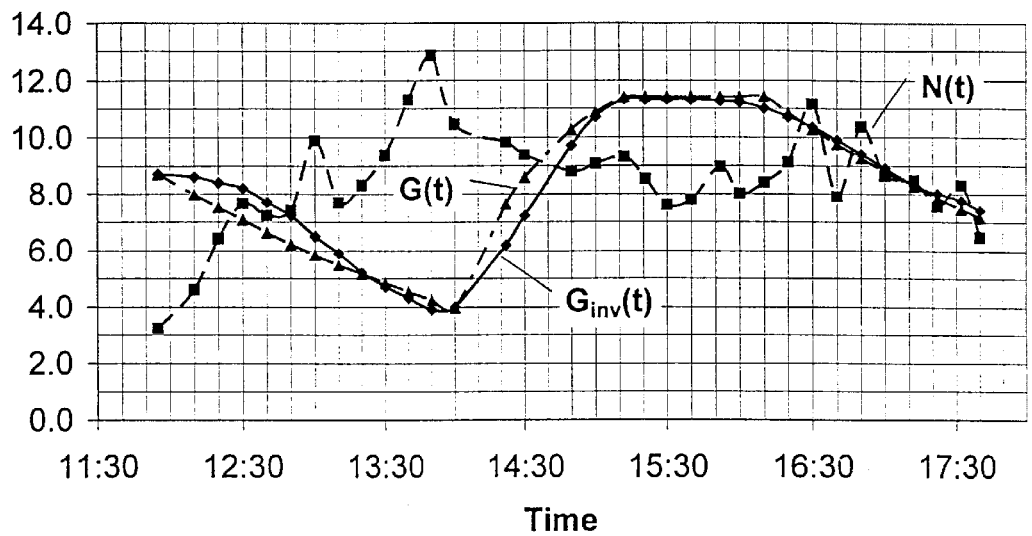
FIG. 1 is a graph illustrating G(t), $G_{inv}(t)$ and N(T) measured for Patient "A" in accordance with the method of the invention.

At the preliminary stage the method provides for simultaneous measurements of the total impedance and the concentration of glucose in blood by any invasive method. The measurements are taken during the increase and during the decrease of the concentration of glucose.

Measurements of the total impedance of the skin or the components of the total impedance can be performed by any suitable method, such as, for example, a method utilizing the radiation of high frequency oscillations and measurements of a resistance with the capacitive sensors. An example of such a device allowing one to perform the measurements by the above-described method is described in the Russian Certificate for a Utility Model #9703.

It is noted that in the present description the term "total electrical resistance" means not only the total impedance comprising the active and reactive components, but also each of the components of the electrical resistance of the skin and percutaneous tissue separately, as well as the combinations or derivatives of these components, such as the ratio of the active resistance over the reactive resistance. The terms "total electrical resistance" and "total impedance" are used throughout this description interchangeably.

To increase the accuracy of an approximation, the preliminary stage measurements are performed for at least two different concentrations below the renal threshold, at approximately the level of the renal threshold, and at least two concentrations above the threshold. The measurements are taken during the increase of the glucose concentration as well as during the decrease of the concentration. Therefore, the measurements of the total electrical resistance and the glucose concentration (by an invasive method) are taken for at least six different ranges of the glucose concentrations:

1) for the concentrations below the renal threshold during the increase of the concentration;

2) for the concentrations around the level of the renal threshold during the increase of the concentration;

3) for the concentrations above the renal threshold during the increase of the concentration;
4) for the concentrations above the renal threshold during the decrease for the concentration;
5) for the concentration around the renal threshold during the decrease of the concentration;
6) for the concentrations below the renal threshold during the decrease of the concentration.

The measurements of the total electrical resistance and the simultaneously measured glucose concentrations serve for the future determination of parameter q and coefficients $a_0$ and $a_1$, correlating the measured total electrical resistance of the skin and the concentration of glucose in blood, which are unique for every individual. A more detailed description of these parameters and how to determine them is provided below. It is important to emphasize that in order to practice the method of the present invention, it is sufficient to perform one cycle of the measurements at the preliminary stage. Nevertheless, a random error of the glucose measurements can be lowered by performing several cycles of the measurements at the preliminary stage.

In order to account for systematic errors, which tend to add up due to various changes happening in a human body over the time period during which the measurement time, it is advisable to repeat the measurements of the preliminary stage periodically (such as once in several months, for example). Nevertheless, accounting for these changes becomes possible by using the results of the measurements of the total electrical resistance in the characteristic concentration regions, such as, for example, the change of the resistance during the transition of over the renal threshold.

In general, the relationship between the total electrical resistance $Z(t)$ and the time-dependent concentration of glucose $G(t)$ can be expressed as the following polynomial:

$$Z(t) = b_{00} + \sum_{j=1}^{M} \sum_{i=0}^{j} b_{ij}(G)^i \left(\frac{dG}{dt}\right)^{j-i} \tag{1}$$

where M is the power of the polynomial (or the degree of approximation of the model used in the calculations, $M \in [1, \infty)$);
  i is the power of the glucose concentration $G(t)$;
  j is the power of the time derivative of the glucose concentration $dG/dt$;
  $b_{ij}$ are the numeric expansion coefficients.

Expression (1) describes a general model correlating the glucose concentration in blood and the total electrical resistance. This general model allows one to describe various specific models conforming to the general one and utilize the corresponding algorithms to determine the concentrations from the total electrical resistance. The accuracy of the calculations based on the expression (1) increases as M increases, which, in turn, might increase the difficulty of the procedure of the glucose determination.

Experimental tests have shown that in order to determine the concentration of glucose with the relative error of 10–15%, it is sufficient to use the model of expression (1) with the approximation of M=1. Expression (1) becomes a linear correlation model of the concentration of glucose and the measured total electrical resistance. That linear model becomes the following:

$$Z(t) = b_{00} + b_{10} G(t) \tag{2}$$

and presents a specific case of an incomplete first order linear model. Such a model leads to an unsatisfactory approximation accuracy.

A complete linear model of the first order of approximation correlating the concentration of glucose and total electrical resistance corresponds to the following expression:

$$Z(t) = b_{00} + b_{10} G(t) + b_{01}(dG(t)/dt). \tag{3}$$

Such a model can be represented by a first order differential equation in the form of:

$$dG(t)/dt + a_0 G(t) = a_1 N(t) + q, \tag{4}$$

using the following substitutes:

$$a_0 = b_{10}/b_{01};$$

$$a_1 = k_r/b_{01};$$

$$q = -b_{00}/b_{01};$$

where $N(t)$ are the measured values of the total electrical resistance of the skin normalized to the value of $G_r$ of the glucose concentration at the moment $t_r$, $t_r$ corresponds to the transition over the renal threshold, where:

$$G_r = N(t_r) = k_r Z(t_r), \tag{5}$$

$k_r$ is the normalization coefficient;

$a_0$—a coefficient characterizing the correlation between the total electrical resistance and the concentration of glucose of a specific individual, the coefficient being generally constant over a long period of time;

q—a parameter that characterizes the ability of a human organism to maintain homeostasis relative to the concentration of glucose in blood (it should be noted that for healthy people q is a non-zero value, while for the insulin-dependent people q is close to zero);

$a_1$—a coefficient accounting for the variability of the external factors and specific features of an organism of a patient. The value of the coefficient also depends on the direction of the change of the glucose concentration in blood. The dependence of the coefficient on the rate of change of the concentration is weak.

The model described by expression (4) is illustrative of the following extreme examples characteristic of the following two groups of people.

Coefficients $a_1 \gg 1$ and $|a_1/a_0| \approx 1$ correspond to a case when the total electrical resistance of the skin is proportional to the glucose concentration, i.e. $N(t) \sim G(t)$. The percentage of the people characterized by such proportionality among the diabetics is not high, although all known methods of determination utilize that model.

In another extreme example, at $|a_0/a_1| \to 0$ and $|a_0| \to 0$, corresponds to a situation when the total electrical resistance of the skin is proportional to the rate of change of the concentration of glucose in blood, i.e. $N(t) \sim dG(t)/dt$. In that case the measured total electrical resistance has numerous maximums and minimums, reflecting the behavior of the rate of change of the concentration.

The above described extreme examples are not encountered frequently in real life. In practice, most of the cases fall between the two extremes.

As a result of solving the differential equation (4), the relation between the glucose concentration and the normalized values of the total electrical resistance can be written as follows:

$$G(t) = G_1 e^{-a_0 t} + q + a_1 e^{-a_0 t} \int_0^t N(x) e^{a_0 x} dx, \qquad (6)$$

where $G_1 = G_0 - q$, $G_0$ is the initial concentration of glucose in blood at the beginning of the measurement process, $N(x)$ are a normalized measured values of the total electrical impedance of the skin or the measured components of the total electrical impedance of the skin.

For the discreet normalized values of the total electrical resistance expression (6) becomes the following:

$$G(t_m) = \qquad (7)$$
$$G_1 e^{-a_0 t_m} + q + a_1 e^{-a_0 t_m} \sum_{k=1}^{m} [N(t_k) e^{a_0 t_k} + N(t_{k-1}) e^{a_0 t_{k-1}}] \frac{(t_k - t_{k-1})}{2},$$

where $t_{k-1}$ and $t_k$ correspond to the times of the discreet measurements, starting with the initial measurement at $t_0=0$, k corresponds to an integer (k=1, 2, . . . m).

Expressions (6) and (7) serve as the working expressions for the procedure of the determining glucose concentration G(t) from the normalized measured values of the total electrical resistance of the skin N(t) during the continuous or discreet measurements. For each individual, parameter q and coefficients $a_0$ and $a_1$ must be determined for the already described ranges of glucose concentrations: above and below the renal threshold for the increasing and decreasing concentrations.

The determination of parameter q and coefficients $a_0$ and $a_1$ is performed by standard mathematical methods, such as for example the minimization of a non-linear functional. The goal of such mathematical processing is to select the values of parameter q and coefficients $a_0$ and $a_1$ for which expression (6) or expression (7) best approximate the experimental results of the measurement of the glucose concentration obtained by an invasive method at the preliminary stage. G(t) measured by an invasive method is taken as "the approximated curve". The results calculated according to expressions (6) and (7) are called here "the approximating curve". The approximation of G(t) by (6) or (7) can be accomplished by using the well-known software product MATLAB, or by any other "off the shelf" software product suitable to perform the approximation. When performing the approximation using MATLAB, first inputting the approximated and the approximating curves into the "curvefit" function of MATLAB should be performed, after which selecting a segment of the approximated curve with a positive slope and the corresponding in time segment of the approximating curve is performed. Finally, the values of parameter q and coefficients $a_0$ and $a_1$ minimizing the deviation between the approximating and approximated curves are found. After that a segment of the approximated curve having a negative slope and a corresponding in time segment of the approximating curve are found. Using the known values of parameter q and coefficient $a_0$, the second value of coefficient $a_1$ minimizing the deviation between the approximating and approximated curves is found.

To calculate normalizing coefficients $k_r$ at the times when the concentration of glucose is approximately equal to $G_r$ (i.e. the concentration at the renal threshold), the corresponding values of the total electrical resistance on the approximating curve are determined. Those determined values are used to calculate the mean arithmetic average and take it as a level $Z(t_r)$ corresponding to the renal threshold. After that coefficients $k_r = G_r/Z(t_r)$ can be calculated.

The method of the present invention provides that after determining $a_0$, q, $a_1$, $k_r$, and the initial glucose concentration $G_0$, only the normalized values of the total electrical resistance N(t) are determined according to $N(t) = k_r Z(t)$. If the measurements are taken continuously, then the concentration of glucose G(t) is calculated according to expression (6). If the measurements are taken discreetly, expression (7) is used, in accordance with the general expression (1) and a selected quantization method (such as a trapezoidal approximation method). To increase the reliability of the measurements of the concentration, it is good to know whether the concentration increases or decreases during a certain time period. The information about the sign of the derivative dG(t)/dt can be obtained by estimating and forecasting the concentration based on the previous measurements, or by statistical processing of the results of the ongoing measurements, or by observing the changes of a shape of an electrocardiosignal related to the changes of glucose concentration in blood.

Importantly, when practicing the method of the present invention, it is possible to correct the values of G(t) without additional invasive glucose measurements. The total electrical resistance of the skin undergoes sharp changes over a short time period around the renal threshold. Such sharp changes allow one to determine the moment of transitioning over the renal threshold based on the behavior of Z(t). Taking into account the fact that for a specific individual the value of $G_r$ was determined at the preliminary measurement stage, the value of N(t) determined for the renal threshold transition time can be substituted for $N(t_r) = G_r$. Therefore, the calculated concentrations G(t) can be corrected without having to repeat the invasive measurements of the preliminary stage. The correction can be performed repeatedly, using only the measurement data of the total electrical resistance, and, in particular, using the information of the concentration corresponding to the renal threshold for a specific individual obtained at the preliminary stage.

It is also contemplated by the present invention that the renal threshold transition time and the corresponding glucose concentration can be determined based on the measurements of some other physiological parameters of an individual, such as, for example, cardiac activity, biological potentials at the acupuncture points etc.

The present invention allows one to determine a necessary insulin injection dosage a patient should inject at a certain moment. The necessary dosage can be determined based on the rate of change of the glucose concentration at a certain moment together with the measurements obtained at the preliminary stage. After injecting the determined dosage of insulin, additional correction of the current values of G(t) can be performed based on the information about the variability of coefficient $a_1$ obtained at the preliminary stage.

The steps of performing the method of the present invention are the following: measuring the total electrical resistance of the skin at the preliminary stage; measuring the glucose concentration in blood using a known invasive method, such as "ONE TOUCH" or "GLUCOTREND" for each measurement of the total resistance. The measurements are taken for the increasing and decreasing glucose concentrations, which can be achieved simply due to the natural daily fluctuations of the glucose, or due to an artificial stimulation through dieting, exercising or an intake of glucose or insulin. It is important to take at least two measurements of the total electrical resistance and concentration during the increase and during the decrease of the glucose concentration in blood. To increase the accuracy of approximating the concentration based on the total resistance, the measurements are taken below, above and approximately at the renal threshold. Accordingly, one should allocate sufficient time for the preliminary stage measurements to record reliable changes of the glucose concentration.

The preliminary stage measurements allow one to obtain the functional relationship between the concentration of glucose and the total electrical resistance of the skin of an individual along with the measurements of the concentration during the increase or decrease cycle. Those measurements are taken as "true" measurements corresponding to the approximation and to the error of the invasive method used at the preliminary stage. Moreover, it is advisable to obtain detailed data of the total electrical resistance and glucose concentration over time especially in the vicinity of the renal threshold. The data obtained in the vicinity of the renal threshold allow one to obtain normalized coefficient $k_r$ using expression (5).

The next steps of the method comprise using the preliminary stage measurements to determine individual coefficients $a_0$, q и $a_1$ for two regions of the glucose concentration: not exceeding the renal threshold and exceeding the renal threshold during the increase and the decrease of the concentration. For the discreet and continuous measurements coefficients $a_0$, q и $a_1$ are determined from the processing of the data obtained at the preliminary stage, as described above.

Before the beginning of the glucose determination process the total electrical resistance is used to determine $G_0$—the initial value relating the resistance and the concentration. After that continuous or discreet measurements of the electrical resistance of the skin are taken and the concentration of glucose is calculated according to expression (6). While measuring the resistance, the resistance data are used to determine the renal threshold and to correct the current calculated value of G(t) by making it equal to $G_r$. If necessary, the correction of G(t) is achieved by taking into account a dosage of medication taken by the patient.

EXPERIMENTAL RESULTS

The method of the present invention was tested on 12 diabetics and 6 non-diabetics. The test group of the diabetics comprised insulin-dependent men and women of the ages 17 to 60 having the diabetic history between 9 and 33 years. Calculations of the glucose concentrations for the group of diabetics were performed in accordance with expression (7) setting q=0.

On the first test day the preliminary stage measurements were performed. The preliminary stage measurements included the determination of the glucose concentration by an invasive method as well as the total impedance of the skin of a finger. The results of the preliminary stage measurements were used to determine coefficients $a_0$ and $a_1$ for two regions of the concentrations: below and above the renal threshold for the increasing and decreasing concentrations. After that the value of $k_r$ was determined.

Turning now to FIG. 1, provided there is the time-dependent glucose concentration data $G_{inv}(t)$ measured invasively for patient "A" on the first day at the preliminary stage. FIG. 1 also provides a graph of the normalized values N(t) of the total impedance with the normalization coefficient being $k_r$=9/400 (approximating function), wherein the numerator 9 mmol/l corresponds to the glucose concentration at the renal threshold for that particular patient, and the denominator 400 Ohm corresponds to the absolute value of the total impedance. The determined coefficients were the following: $a_0$=0.005; $a_1 \approx$−0,0018 (for the entire concentration decrease region); $a_1 \approx$+0,0215 (for the entire concentration increase region). A graph illustrating the calculated values of G(t) obtained from expression (7) with the determined values of those coefficients and the quality of correction typical for the preliminary stage measurements is also provided in FIG. 1. As follows from FIG. 1, relative deviations of the calculated function from the approximated function do not exceed 20% while the average deviation of the absolute value does not exceed 10%.

During the subsequent test days the concentration of glucose G(t) was determined by taking discreet measurements of the total impedance of the skin of a finger with an interval between the measurements from 2 days to 3 months. Calculating G(t) is done using expression (7) and coefficients $k_r$, $a_0$ and $a_1$ together with the initial concentration $G_0$ obtained at the preliminary stage. To determine the error of the method of the present invention, the parallel determination of the glucose concentrations were performed by an invasive method. The error of the method ranged from about 8% to about 17% for different patients, with an average error of about 11%.

The present method was compared to the already known method described in the Russian Certificate for a Utility Model #9703. The error of that method according to the data provided in the Certificate is about 32%, which is probably due to the fact that method does not take into account the effect caused by the rate of change of the concentration on the total impedance.

Figure 2:
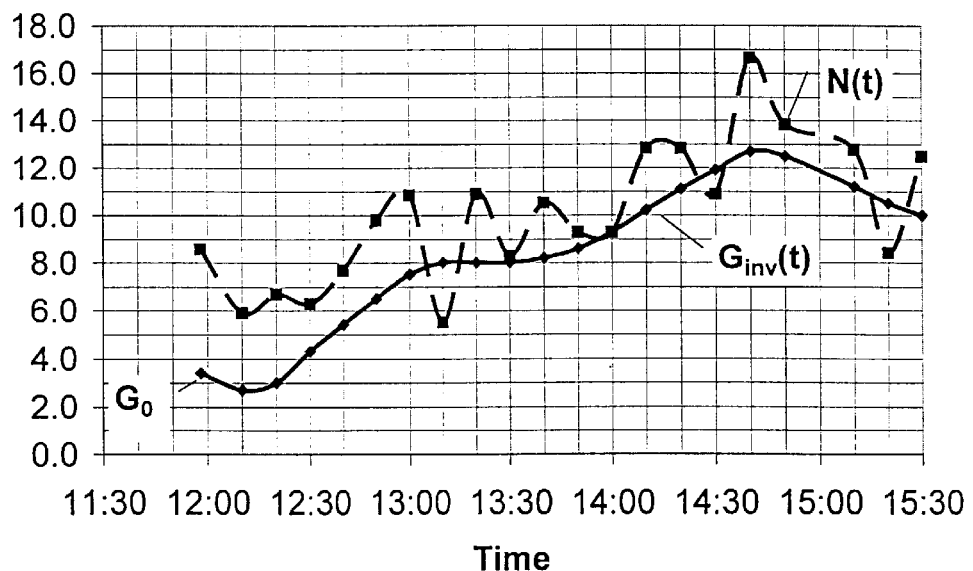
FIG. 2–FIG. 5 are the graphs illustrating the results of the measurements for Patient "A" during one of the test days.
Figure 3:
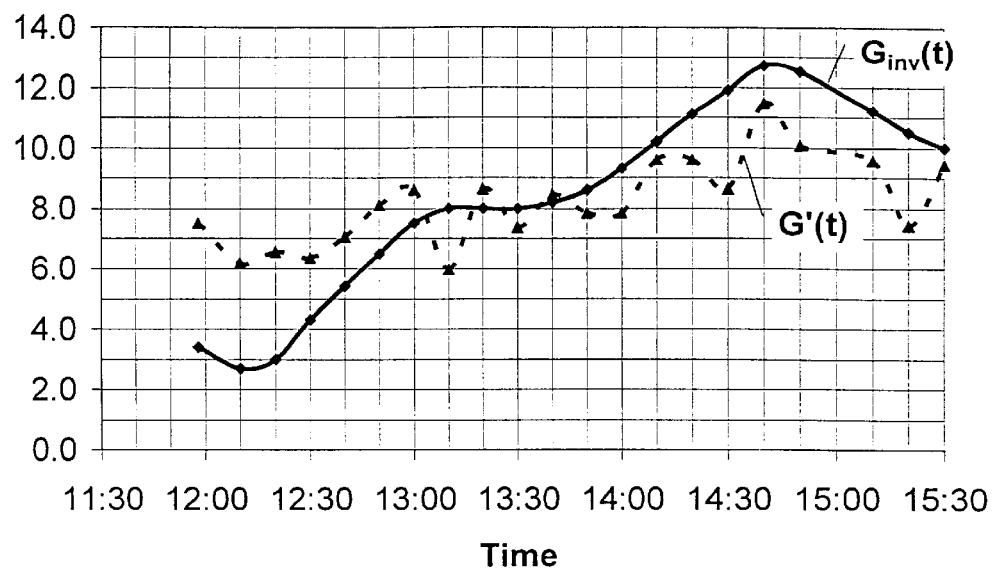
Figure 4:
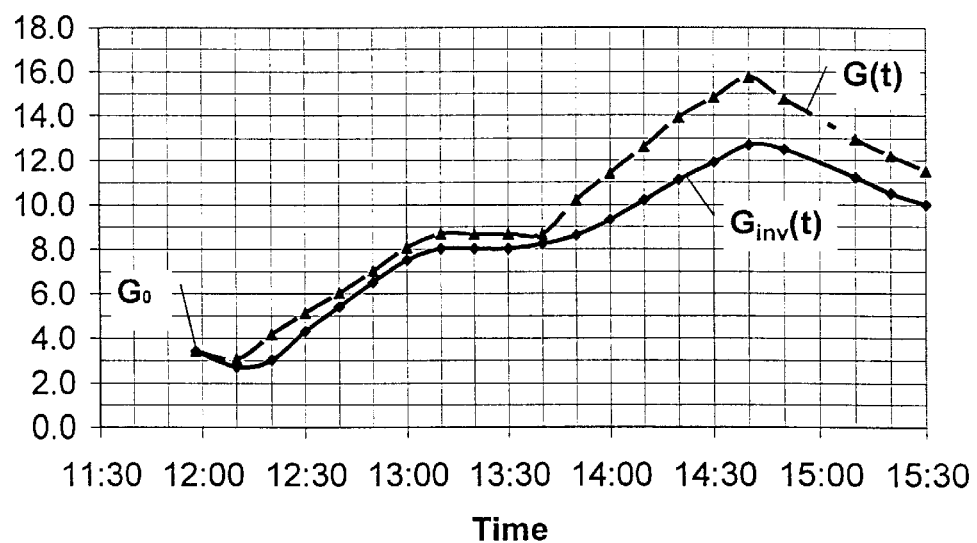

The experimental results for patient "A" obtained during one of the test days are provided in FIGS. 2–5. FIG. 2 shows the graphs for $G_{inv}(t)$ and N(t) corresponding to that test day. FIG. 3 provides the calculated values for G'(t) according to the method described in Certificate #9703. FIG. 4 provides the data for G(t) obtained using the method of the present invention. For comparison purposes, FIGS. 3 and 4 also show the data corresponding the glucose concentrations $G_{inv}(t)$ obtained by an invasive method.

As follows from these graphs, the function for total impedance does not coincide with the function for the concentration determined by an invasive method (FIG. 2), therefore the known method for determining the concentration of glucose G'(t) (FIG. 3) has a significant error.

At the same time, it can be seen that the concentration of glucose G(t) determined in accordance with the method of the present invention (FIG. 4) provides good correlation between G(t) and the data for the glucose concentration $G_{inv}(t)$ obtained by an invasive method.

Figure 5:
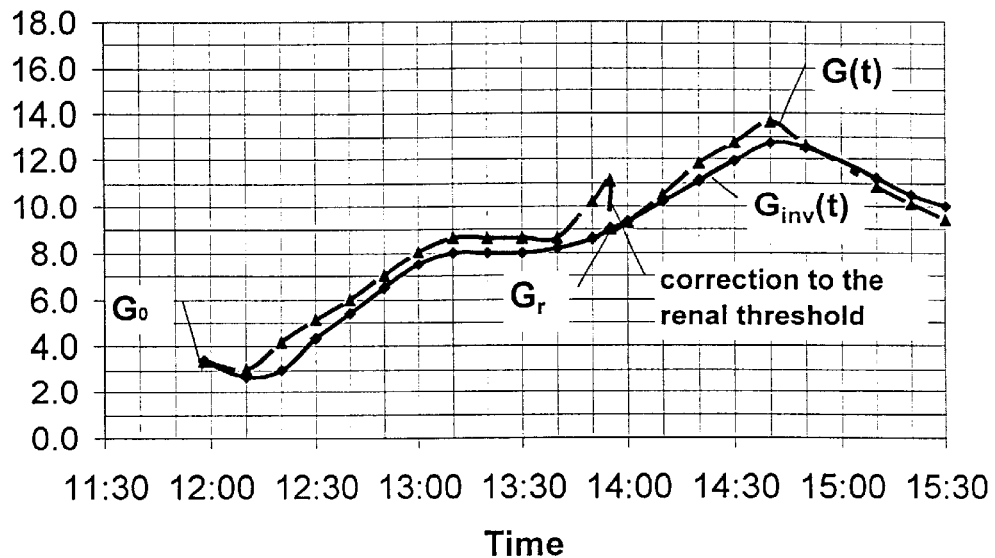

FIG. 5 shows an example of correction of the glucose concentration data G(t) with respect to the renal threshold. As follows from FIG. 5, the correction makes it possible to increase the accuracy of the determination of the glucose concentration.

Figure 6:
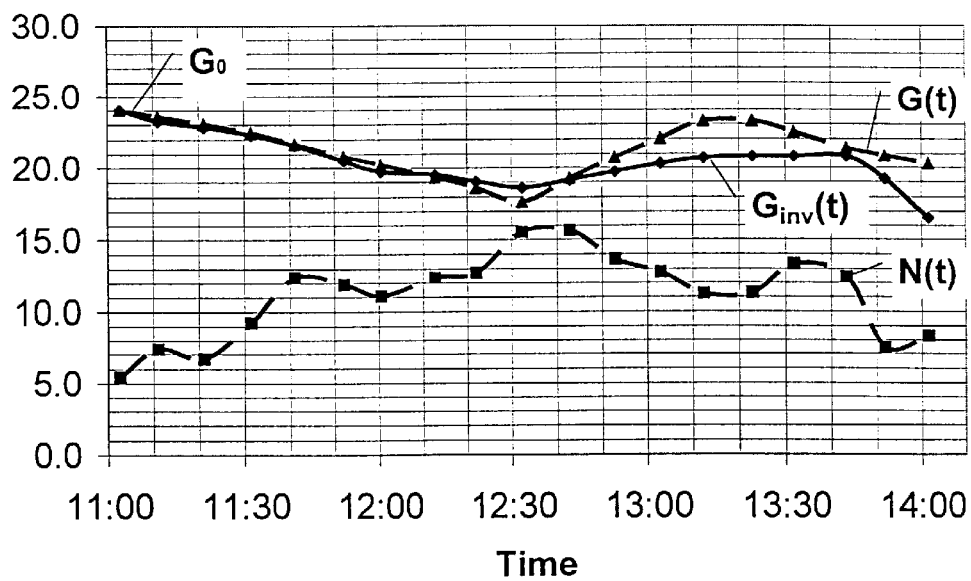
FIG. 6 is a graph illustrating the results of the measurements for Patient "B".
Figure 7:
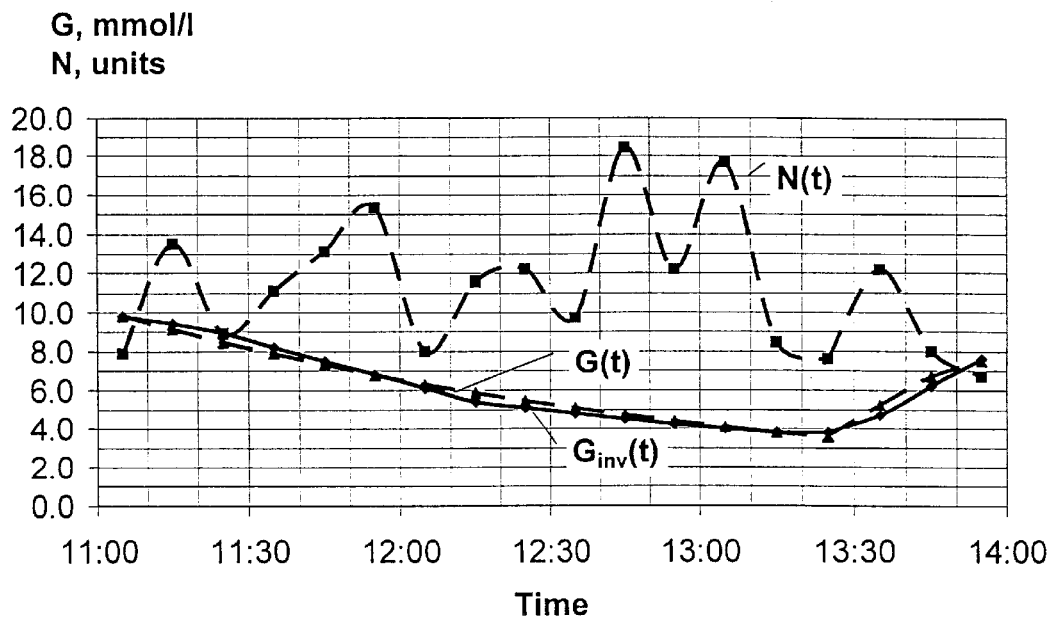
FIG. 7–FIG. 8 are the graphs illustrating the measurement results for Patient "C".
Figure 8:
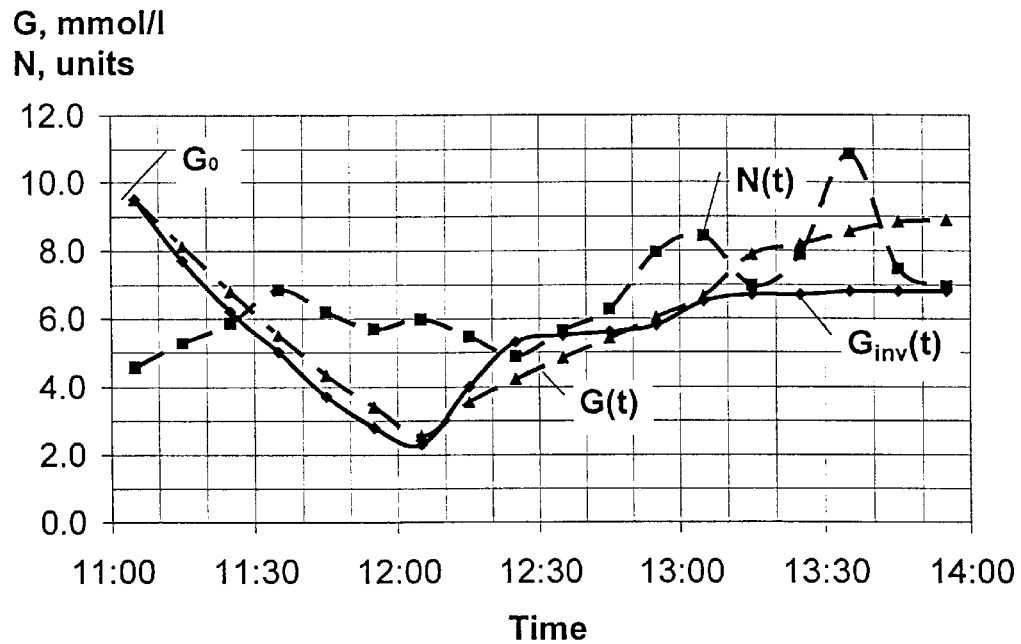

FIGS. 6–8 show the results of the measurements of the total impedance N(t) and the calculated glucose concentrations G(t) for patient "B" (FIG. 6) and patient "C" (FIG. 7 and FIG. 8). Each of these figures provides normalized data for the total impedance N(t), the glucose concentration data G(t) calculated according to the method of the present invention, and the glucose concentration data $G_{inv}(t)$ determined by an invasive method. The graphs in FIGS. 7–8 illustrate the differences in the decrease rate of the glucose concentration for the same patient without an insulin injection (FIG. 7) and after an insulin injection (FIG. 8). The injection of insulin was accompanied by the correction of coefficient $a_1$ in expression (7), taking into account the

What is claimed is:

1. A method of determining glucose concentration G(t) in blood comprising:
   a) at a preliminary measurement stage, measuring the values of impedance or a component of impedance between the electrodes placed on the skin of a patient and invasively measuring the values of a glucose concentration $G_{inv}(t)$ of the patient;
   b) determining parameters $a_0$, q and $a_1$ in an expression $$G(t) = G_1 e^{-a_0 t} + q + a_1 e^{-a_0 t} \int_0^t N(x) e^{a_0 x} dx;$$

by using the measured values of impedance or the component of impedance and the measured values of the glucose concentration $G_{inv}(t)$ and approximating $G_{inv}(t)$ to G(t); and
   c) independently of when and where steps a) and b) were performed, non-invasively measuring impedance or a component of impedance between electrodes placed on the skin of the patient and calculating the glucose concentration G(t) according to the expression, wherein step c) can be repeated without repeating steps a) and b).

2. The method wherein step a) occurs over a 1, wherein time interval T is sufficient to observe the changes of glucose concentration related to the natural daily variations of the glucose concentration and the changes related to a diet, exercise, glucose or insulin injections.

3. The method of claim 1, further comprising performing preliminary stage measurements during an increase of the glucose concentration.

4. The method of claim 1, further comprising performing preliminary stage measurements during a decrease of the glucose concentration.

5. The method of claim 1, further comprising determining the parameters $a_0$, q and $a_1$, for the glucose concentrations below, above and approximately at a renal threshold of a patient.

6. The method of claim 1, further comprising correcting the glucose concentration G(t) at the renal threshold by making the G(t) equal to a value of the glucose concentration at the renal threshold obtained by the invasive method at the preliminary stage.

7. The method of claim 1, wherein measuring impedance comprises measuring a reactive component of the total impedance, an active component of impedance, or a phase angle between the reactive and the active components.

8. The method of claim 1, wherein q=0 for an insulin-dependent patient.

9. The method of claim 2, wherein the time interval T is between about 4 hours and about 12 hours.

10. A method of determining glucose concentration $G(t_m)$ in blood of comprising:
    a) at a preliminary measurement stage, measuring the values of impedance or a component of impedance between the electrodes placed on the skin of a patient and invasively measuring the values of a glucose concentration $G_{inv}(t)$ of the patient;
    b) determining parameters $a_0$, q and $a_1$ in an expression $$G(t_m) = G_1 e^{-a_0 t_m} + q + a_1 e^{-a_0 t_m} \sum_{k=1}^{m} [N(t_k) e^{a_0 t_k} + N(t_{k-1}) e^{a_0 t_{k-1}}] \frac{(t_k - t_{k-1})}{2};$$

by using the measured values of impedance or the component of impedance and the measured values of the glucose concentration $G_{inv}(t)$ and approximating $G_{inv}(t)$ to $G(t_m)$; and
    c) independently of when and where steps a) and b) were performed, non-invasively measuring impedance or a component of impedance between electrodes placed on the skin of the patient and calculating the glucose concentration $G(t_m)$ according to the expression, wherein step c) can be repeated without repeating steps a) and b).

11. The method of claim 10, wherein step a) occurs over a time interval T is sufficient to observe the changes of glucose concentration related to the natural daily variations of the glucose concentration and the changes related to a diet, exercise, glucose or insulin injections.

12. The method of claim 10, further comprising performing preliminary stage measurements during an increase of the glucose concentration.

13. The method of claim 10, further comprising performing preliminary stage measurements during a decrease of the glucose concentration.

14. The method of claim 10, further comprising determining the parameters $a_0$, q and $a_1$ for the glucose concentrations below, above and approximately at a renal threshold of a patient.

15. The method of claim 10, further comprising correcting the glucose concentration $G(t_m)$ at the renal threshold by making the $G(t_m)$ equal to a value of the glucose concentration at the renal threshold obtained by the invasive method at the preliminary stage.

16. The method of claim 10, wherein measuring impedance comprises measuring a reactive component of the total impedance, an active component of impedance, or a phase angle between the reactive and the active components.

17. The method of claim 10, wherein q=0 for an insulin-dependent patient.

18. The method of claim 11, wherein the time interval T is between about 4 hours and about 12 hours.

* * * * *